United States Patent [19]

McCook et al.

[11] Patent Number: 5,382,432
[45] Date of Patent: Jan. 17, 1995

[54] COSMETIC METHOD FOR TREATMENT OF SKIN

[75] Inventors: John P. McCook, Guilford; Alan J. Meyers, Trumbull; Anthony Vargas, Monroe, all of Conn.

[73] Assignee: Elizabeth Arden Company, Division of Conopco, Inc., New York, N.Y.

[21] Appl. No.: 152,151

[22] Filed: Nov. 15, 1993

[51] Int. Cl.$^6$ ............................................. A61K 7/48
[52] U.S. Cl. .................................. 424/401; 514/844; 514/847
[58] Field of Search ................. 424/401; 514/844, 847

[56] References Cited

U.S. PATENT DOCUMENTS

| | | | |
|---|---|---|---|
| 4,105,782 | 8/1978 | Yu et al. | 424/283 |
| 4,105,783 | 8/1978 | Yu et al. | 424/283 |
| 4,197,316 | 4/1980 | Yu et al. | 424/317 |
| 4,234,599 | 11/1980 | Van Scott et al. | 424/279 |
| 4,424,234 | 1/1984 | Alderson et al. | 424/317 |
| 5,091,171 | 2/1992 | Yu et al. | 424/642 |

Primary Examiner—Thurman K. Page
Assistant Examiner—Jyothsna Venkat
Attorney, Agent, or Firm—Milton L. Honig

[57] ABSTRACT

A method is provided for improving skin condition through a system whose steps include applying to the skin separately on a plurality of days a first composition that incorporates a $C_2$–$C_{28}$ α- or β-hydroxy carboxylic acid in a pharmaceutically acceptable carrier. Once the skin has acclimated to any irritation induced by the first composition, a second composition is applied to the skin daily for a subsequent period of time. The second composition will also include hydroxy carboxylic acid but at a level at least about 10% higher than that employed in the first composition. Once the skin has acclimated to the second composition, subsequent progressive increases of the active hydroxy carboxylic acid can be applied over subsequent periods of time Finally, a maintenance level composition is utilized with the highest level of hydroxy carboxylic acid in the progressive program to minimize potential irritation.

10 Claims, No Drawings

COSMETIC METHOD FOR TREATMENT OF SKIN

BACKGROUND OF THE INVENTION

1. Field of the Invention

The invention concerns a method to combat the appearance of wrinkles and other signs of aging through a progressive regimen of α- or β-hydroxy carboxylic acid skincare.

2. The Related Art

A soft, supple and flexible skin has a marked cosmetic appeal and is an attribute of normal functioning epidermis. As human skin ages with advancing years, the epidermis can become folded, ridged or furrowed to form wrinkles. These signal loss of youthful appearance and herald the transition to old age. Exposure to excessive doses of sunlight accelerates the transition process. Also, the outer layer of the epidermis known as the stratum corneum can become dry and flaky following exposure to cold weather or excessive contact with detergents or solvents. Loss of skin moisture thereby results and the skin begins to lose the soft, supple and flexible characteristics.

Emollients such as fats, phospholipids and sterols have in the past been used to soften wrinkled or dry skin. These emollients are only partially effective as a remedy for skin in poor condition.

The use of hydroxy carboxylic acids for enhancing the quality of human skin has been known for some time. There is no doubt that α-hydroxy carboxylic acids are therapeutically effective much beyond the common emollients.

U.S. Pat. No. 4,424,234 (Alderson et al.) discloses skin treatment compositions incorporating α-hydroxycaproic acid and α-hydroxycaprylic acid or mixtures thereof in compositions that have a pH value of less than 7, usually from 2 to 4. Yu and Van Scott have patented widely in this area. For instance, U.S. Pat. No. 4,105,782 reports amines or ammonium salts of α-hydroxy carboxylic acids in the treatment of acne or dandruff. In U.S. Pat. No. 4,105,783 and U.S. Pat. No. 4,197,316, these compounds are suggested for the treatment of dry skin. U.S. Pat. No. 4,234,599 discloses the use of α-hydroxy carboxylic acids, their esters or amine salts in the treatment of keratoses. More recently, U.S. Pat. No. 5,091,171 focused attention on these compounds as being effective against age spots, wrinkles and aging related skin changes.

While hydroxy carboxylic acids hold much therapeutic promise, these materials have been found to irritate human skin on repeated topical applications. The irritation may range from a sensation of tingling, itching and burning to clinical signs of redness and peeling. Causes for such irritation have been linked to the lowering of pH in the stratum corneum of human skin. Low pH has been suggested as provoking disturbances in intercorneocyte bondings resulting in adverse skin reactions, specially in some individuals with sensitive skin.

Accordingly, it is an object of the present invention to provide a method for improving skin condition through application of α- or β-hydroxy carboxylic acids in a treatment regimen that eliminates irritation, especially the sensation of tingling, itching and burning as well as redness and peeling.

Another object of the present invention is to provide a method for improving skin condition in a treatment regimen wherein fine lines and wrinkles appear visibly reduced; texture, softness and smoothness are dramatically improved; and skin firmness and elasticity become noticeably stronger.

These objects and others will become more apparent from consideration of the following summary and detailed description.

SUMMARY OF THE INVENTION

A method for improving skin condition is provided through a system whose steps include:

(i) applying to the skin separately on a plurality of days a first composition including:
- from about 0.0001 to 20% of a $C_2$–$C_{28}$ α- or β-hydroxy carboxylic acid; and
- from about 1 to 99.9% of a first pharmaceutically acceptable carrier;

(ii) applying to the skin, after completion of all treatments in step (i), separately on a plurality of further days a second composition including:
- from about 0.0002 to 20% of a $C_2$–$C_{28}$ α- or β-hydroxy carboxylic acid identical to but at a concentration at least about 10% higher than that employed in step (i); and
- from about 1 to 99.9% of a second pharmaceutically acceptable carrier.

The method may further include a step (iii) involving applying to the skin, after completion of all treatments in step (ii), separately on a plurality of further days a third composition including:
- from about 0.0003 to 20% of a $C_2$–$C_{28}$ α- or β-hydroxy carboxylic acid identical to but at a concentration at least about 10% higher than that employed in step (ii); and
- from about 1 to 99.9% of a third pharmaceutically acceptable carrier.

The method may include a still further step (iv) involving applying to the skin after completion of all treatments in step (iii), separately on a plurality of still further days a fourth composition including:
- from about 0.0004 to 20% of a $C_2$–$C_{28}$ α- or β-hydroxy carboxylic acid identical to but at a concentration at least about 10% higher than that employed in step (iii); and
- from about 1 to 99.9% of a fourth pharmaceutically acceptable carrier;

and step (v) involving maintaining treatment of step (iv) for a period of days whose total is longer than the days in any of steps (i), (ii) or (iii), thereby becoming the final step in a progressive program to acclimate skin to any potential irritation imparted by the α- or β-hydroxy carboxylic acid.

In a preferred embodiment of the invention, the first through fourth pharmaceutically acceptable carriers are all constituted of identical components in essentially identical concentrations. Only concentrations of the α- or β-hydroxy carboxylic acid, as well as slight modifications of the major carrier to complement concentration changes on a qs basis, are the only variables for the preferred embodiment in formulating the compositions.

DETAILED DESCRIPTION OF THE INVENTION

Intolerance to $C_2$–$C_{28}$ α- or β-hydroxy carboxylic acids can now be overcome through a progressive program of treatment which allows acclimation to increasing levels of the acid.

Typically, the program is conducted over six weeks. For the first two weeks, a low level of hydroxy carboxylic acid containing first composition is daily applied to the skin, particularly the face. Levels of the acid may range from about 0.0001 to 20%, preferably from about 0.1 to 3%, optimally about 2% by weight.

From the third through the fourth week, treatment is conducted with a second composition containing the identical hydroxy carboxylic acid, except at a concentration at least about 10% higher than that employed in weeks 1-2. Levels of the acid may range from about 0.0002 to 20%, preferably from about 0.2 to 5%, optimally about 3% by weight. Application is again performed on a once-daily basis.

From the fifth through the sixth week, daily treatment is conducted with a third composition containing a hydroxy carboxylic acid identical to that used in the previous compositions but at a concentration at least about 10% higher than in weeks 3-4. Levels of the acid may range from about 0.0003 to 20%, preferably from about 0.3 to 8%, optimally about 4% by weight.

From the seventh week onward, treatment is conducted with a fourth and final or maintenance composition containing hydroxy carboxylic acid identical to that employed in the previous compositions but at a concentration at least about 10% higher than that present in the third composition. Levels of acid may range from about 0.0004 to 20%, preferably from about 0.4 to 12%, optimally about 5% by weight. This final step in the progressive program is conducted daily for at least two months whereupon noticeable improvements in skin appearance will occur. Once acclimated by the starter system of compositions 1-3, the maintenance composition 4 can be applied for any extended length of days.

A wide variety of $\alpha$-hydroxy carboxylic acids may be employed for purposes of the present invention. Suitable examples include:

$\alpha$-hydroxyethanoic acid
$\alpha$-hydroxypropanoic acid
$\alpha$-hydroxyhexanoic acid
$\alpha$-hydroxyoctanoic acid
$\alpha$-hydroxydecanoic acid
$\alpha$-hydroxydodecanoic acid
$\alpha$-hydroxytetradecanoic acid
$\alpha$-hydroxyhexadecanoic acid
$\alpha$-hydroxyoctadecanoic acid
$\alpha$-hydroxyeicosanoic acid
$\alpha$-hydroxydocosanoic acid
$\alpha$-hydroxyhexacosanoic acid, and
$\alpha$-hydroxyoctacosanoic acid Particularly preferred from the above list are $\alpha$-hydroxyethanoic acid (commonly known as glycolic acid), $\alpha$-hydroxypropanoic acid (commonly known as lactic acid) and $\alpha$-hydroxyoctanoic acid (commonly known as $\alpha$-hydroxycaprylic acid or HCA).

Illustrative and most preferred of the $\beta$-hydroxy carboxylic acids is salicylic acid.

For purposes of this invention, the term $\alpha$- or $\beta$- hydroxy carboxylic acids are intended to include not only the acid form but also salts thereof. Typical salts are the alkalimetal, ammonium and $C_2$-$C_{30}$ ammonium salts thereof. Particularly preferred are the sodium, potassium, triethanolammonium and ammonium salts. Combinations of all the foregoing may be present in the compositions.

A wide variety of pharmaceutically acceptable carriers may be utilized for the present invention. Amounts of the carrier may range from about 1 to 99.9%, preferably from about 80 to 98%, optimally between about 90 and 95% by weight.

Compositions of the present invention are preferably anhydrous (less than 2% but preferably less than 0.5% water) but may also be aqueous. When water is present, the product form may be as an emulsion in the form of a lotion or cream.

Among other types of pharmaceutically acceptable carriers may be silicone oils. Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients.

Silicones may be present in amounts ranging from about 0.1 up to about 60%, preferably from about 2 to about 25%, optimally between about 10 and 20% by weight.

Synthetic esters are a further category of possible pharmaceutically acceptable carriers which can also be utilized as emollients within compositions of the invention. Among the suitable esters are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}-C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Fatty alcohols and fatty acids include those compounds having from 10 to 20 carbon atoms may be utilized as carriers for purposes of the present invention. Especially preferred are such compounds as cetyl, myristyl, palmityl, isostearyl and stearyl alcohols and acids.

Surfactants, which are also sometimes designated as emulsifiers, may be incorporated into the cosmetic compositions of the present invention. Surfactants can comprise anywhere from about 0.5 to about 30%, preferably from about 1 to about 15% by weight of the total composition. Surfactants may be cationic, nonionic, anionic or amphoteric in nature and combinations thereof may be employed.

Illustrative of the nonionic surfactants are alkoxylated compounds based upon fatty alcohols, fatty acids and sorbitan. These materials are available, for instance, from the Shell Chemical Company under the "Neodol" designation. Copolymers of polyoxypropylene-polyoxyethylene, available under the Pluronic trademark sold by the BASF Corporation, are sometimes also useful. Alkyl polyglucosides available from the Henkel Corporation similarly can be utilized for the purposes of this invention.

Anionic-type surfactants may include fatty acid soaps, sodium lauryl sulphate, sodium lauryl ether sulphate, alkyl benzene sulphonate, mono and dialkyl acid phosphates and sodium fatty acyl isethionate.

Amphoteric surfactants include such materials as dialkylamine oxide and various types of betaines (such as cocoamido propyl betaine).

Another category of functional ingredients within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Skin active agents other than $\alpha$- or $\beta$-hydroxy carboxylic acids may also be included in compositions of the present invention. These actives may include sunscreens, tanning agents, anti-acne agents and adjunct anti-wrinkle inhibitors. Among the latter category are ceramides which are N-acylated sphingosine bases. Especially preferred are ceramide 1, ceramide 2 and ceramide 3. Identity of these materials are well-outlined in "Advances in Lipid Research," Vol. 24, pgs. 27–56, by Schurer and Elias (1991). Levels of ceramide may range from 0.00001 to 1% by weight.

Vitamins may also be included in the compositions of the present invention. Especially preferred is vitamin A palmitate (retinyl palmitate) and vitamin E linoleate (tocopheryl linoleate). Other esters of vitamins A and E may also be utilized.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, proprionate salts, and a variety of quaternary ammonium compounds.

Particularly preferred preservatives are methyl paraben, propyl paraben, imidazolidinyl urea, sodium dehydroxyacetate and benzyl alcohol. Preservatives will usually be employed in amounts ranging from about 0.1% to 2% by weight of the composition.

Powders may be incorporated into the cosmetic compositions of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these materials may range anywhere from 0.001 up to 20% by weight of the composition.

The following examples will more fully illustrate selected embodiments of this invention. All parts, percentages and proportions referred to herein and in the appended claims are by weight unless otherwise indicated.

EXAMPLE 1

This example illustrates a treatment system according to the present invention. Daily for two weeks, starter composition 1 is applied to the face. For a subsequent two weeks, starter composition 2 is applied daily to the face. After the fourth week, starter composition 3 is applied daily to the face for a successive two weeks. Finally, maintenance composition 4 is applied daily to the face beginning at the seventh week and continued for at least two months. Components and weight percent concentrations of the aforementioned compositions are outlined in Table 1: below.

TABLE I

| COMPONENT | Starter Composition System (Weight %) | | | Maintenance Composition |
|---|---|---|---|---|
| | 1 | 2 | 3 | 4 |
| l-Lactic Acid | 2.00 | 3.00 | 4.00 | 5.00 |
| Potassium l-Lactate | 0.93 | 1.41 | 1.88 | 2.34 |

TABLE I-continued

| COMPONENT | Starter Composition System (Weight %) | | | Maintenance Composition |
| --- | --- | --- | --- | --- |
| | 1 | 2 | 3 | 4 |
| Isostearyl Neopentanoate | 36.50 | 35.01 | 33.54 | 32.08 |
| PEG-8 Caprylic/Capric Glycerides | 14.30 | 14.30 | 14.30 | 14.30 |
| Cetyl Octanoate | 12.75 | 12.75 | 12.75 | 12.75 |
| Polyglyceryl-6 Dioleate | 11.90 | 11.90 | 11.90 | 11.90 |
| Cyclomethicone | 10.17 | 10.17 | 10.17 | 10.17 |
| PPG-5-Ceteth-20 | 5.10 | 5.10 | 5.10 | 5.10 |
| Glyceryl Isostearate | 3.13 | 3.13 | 3.13 | 3.13 |
| Hydroxycaprylic Acid | 0.01 | 0.01 | 0.01 | 0.01 |
| Ceramide 3 | 0.01 | 0.01 | 0.01 | 0.01 |
| Ceramide 2 | 0.01 | 0.01 | 0.01 | 0.01 |
| Water | qs | qs | qs | qs |

EXAMPLE 21

This example illustrates another treatment system according to the present invention. Daily for two weeks, starter composition 1 is applied to the face. For a subsequent two weeks, starter composition 2 is applied daily to the face. After the, fourth week, starter composition 3 is applied daily to the face for a successive two weeks. Finally, maintenance composition 4 is applied daily to the face beginning at the seventh week and continued for at least two months. Components and weight percent concentrations of the aforementioned compositions are outlined in Table II below.

TABLE II

| COMPONENT | Starter Composition (Weight %) | | Maintenance Composition |
| --- | --- | --- | --- |
| | 1 | 2 | 3 |
| Salicylic Acid | 3.10 | 5.20 | 8.00 |
| Isopropyl Octanoate | 40.75 | 38.65 | 35.85 |
| PEG-8 Caprylic/Capric Glycerides | 16.30 | 16.30 | 16.30 |
| Cyclomethicone | 14.15 | 14.15 | 14.15 |
| Sorbitan Monooleate | 10.90 | 10.90 | 10.90 |
| Isostearic Acid | 5.34 | 5.34 | 5.34 |
| Xanthan Gum | 0.10 | 0.10 | 0.10 |
| Ceramide 3 | 0.01 | 0.01 | 0.01 |
| Ceramide 2 | 0.01 | 0.01 | 0.01 |
| Water | qs | qs | qs |

EXAMPLE 3

Clinical studies were conducted in accordance with the treatment method of the present invention. The study involved cells of 25 panelists each per treatment system. These panelists were females, 30–55 years of age, whose skin indicated slight to moderate signs of photo damage. During the study the panelists applied product twice a day to designated areas of the face, chest and legs. A control product (without l-lactic acid) was applied to adjacent areas of the face, chest and legs. Assessments were conducted at stages of 2, 4, 6 and 8 weeks. These assessments included a self-assessment by the panelist as well as an expert evaluation for adverse reactions to the tested products. Self-assessment included reports of itchiness, pimples, redness, burning, rash, dryness and the like.

The test formulations were those outlined under Table I, except that the l-lactic acid concentration was altered in accordance with that reported under Table II.

TABLE II
COMPARATIVE STUDY

| FORMULATION | WEEKS | NO. OF ADVERSE REACTIONS |
| --- | --- | --- |
| Cell 1 | | |
| 2% Lactic Acid | 0–2 | 6 |
| 3% Lactic Acid | 2–4 | 8 |
| 4% Lactic Acid | 4–6 | 9 |
| 5% Lactic Acid | 6–8 | 6 |
| Cell 2 (Control) | | |
| 5% Lactic Acid | 0–2 | 29 |
| 5% Lactic Acid | 2–4 | 5 |
| 5% Lactic Acid | 4–6 | 4 |
| 5% Lactic Acid | 6–8 | 6 |
| Cell 3 | | |
| 2.5% Lactic Acid | 0–2 | 8 |
| 5% Lactic Acid | 2–4 | 7 |
| 7.5% Lactic Acid | 4–6 | 4 |
| 10% Lactic Acid | 6–8 | 6 |
| Cell 4 (Cotrol) | | |
| 10% Lactic Acid | 0–2 | 32 |
| 10% Lactic Acid | 2–4 | 20 |
| 10% Lactic Acid | 4–6 | 22 |
| 10% Lactic Acid | 6–8 | 22 |

The 25 panelists of Cell 1 applied in a progressive manner increasing levels of lactic acid which began at 2% for the first two weeks. Over weeks 2–4 and 4–6, the active level was raised to 3 and 4%, respectively. Finally, a maintenance level of 5% was reached during weeks 6–8. The number of adverse reactions remained at a fairly constant and low level (less than 10 adverse reactions).

Cell 2 was a control test. Throughout the 8 week period, the 25 panelists applied an identical 5% level of lactic acid. An extremely high level of adverse reactions (29) was observed during the initial two week period. Only after the initial period did the number of adverse reactions subside. Evident from this result is the severe response encountered with $\alpha$-hydroxy carboxylic acids when skin is first exposed to such treatment. By contrast, the progressive method practiced with Cell 1 eliminated the burst of adverse response.

Cell 3 followed the regimen of Cell 1 except that 2.5% lactic acid was utilized over the first two weeks. Thereafter, the level of active was raised for weeks 2–4 and 4–6 to 5% and 7.5%, respectively. Finally, a maintenance level of 10% lactic acid was reached at the 6–8 week period. No sharply adverse number of reactions were found. By contrast, Cell 4 employed as a control 10% lactic acid applied throughout the 8 week clinical evaluation. A very high number of adverse reactions were noted initially (32) and this level continued at a fairly high level throughout the remainder of the test period.

The foregoing examples illustrated only selected embodiments of the present invention and should be considered nonlimiting examples with variations and modifications thereof all being within the spirit and purview of this invention.

What is claimed is:

1. A method for improving skin condition with a system whose steps comprise:
   (i) applying to the skin separately on a plurality of days a first composition comprising:
      from about 0.0001 to 20% of an $\alpha$-hydroxy carboxylic acid selected from the group consisting of lactic acid, glycolic acid, $\alpha$-hydroxycaprylic acid and combinations thereof or a $\beta$-hyudroxycarboxylic acid which is salicylic acid; and from about 1 to 99.9% of a first pharmaceutically acceptable carrier;

(ii) applying to the skin, after completion of step (i), a second composition separately on a plurality of further days comprising:

from about 0.0002 to 20% of an α-hydroxy carboxylic acid selected from the group consisting of lactic acid, glycolic acid, α-hydroxycaprylic acid and combinations thereof or a β-hydroxycarboxylic acid which is salicylic acid, the hydroxy carboxylic acid being identical to but at a concentration at least about 10% higher than that employed in step (i); and from about 1 to 99.9% of a second pharmaceutically acceptable carrier.

2. A method according to claim 1 further comprising:

(iii) applying to the skin, after completion of step (ii), a third composition separately on a plurality of further days comprising:

from about 0.0003 to 20% of an α-hydroxy carboxylic acid selected from the group consisting of lactic acid, glycolic acid, α-hydroxycaprylic acid and combinations thereof or a β-hydroxycarboxylic acid which is salicylic acid, the hydroxy carboxylic acid being identical to but at a concentration at least about 10% higher than that employed in step (ii); and from about 1 to 99.9% of a third pharmaceutically acceptable carrier.

3. A method according to claim 2 further comprising:

(iv) applying to the skin, after completion of step (iii), a fourth composition separately on a plurality of further days comprising:

from about 0.0004 to 20% of an α-hydroxy carboxylic acid selected from the group consisting of lactic acid, glycolic acid, α-hydroxycaprylic acid and combinations thereof or a β-hydroxycarboxylic acid which is salicylic acid, the hydroxy carboxylic acid being identical to but at a concentration at least about 10% higher than that employed in step (iii);

(v) maintaining step (iv) for a period of days whose total is longer than the days in any of steps (i), (ii) or (iii), thereby becoming the final step in a progressive program to acclimate skin to any potential irritation imparted by the hydroxy carboxylic acid.

4. A method according to claim 3 wherein the first through fourth compositions have identical components at identical concentrations except that the hydroxy carboxylic acid concentrations are different among different compositions and that the concentration of the respective pharmaceutically acceptable carriers are accordingly adjusted to accommodate any concentration changes of the hydroxy carboxylic acid.

5. A method according to claim 1 wherein the α- or β-hydroxy carboxylic acid of step (i) is present from 0.1 to 3% and in step (ii) is present from 0.2 to 5%.

6. A method according to claim 5 wherein the α-hydroxy carboxylic acid is lactic acid and is present at a level of 2% in step (i) and at 3% in step (ii).

7. A method according to claim 2 wherein the α- or β-hydroxy carboxylic acid of step (iii) is present from 0.3 to 8%.

8. A method according to claim 7 wherein the α-hydroxy carboxylic acid of step (iii) is lactic acid and is present therein at 4%.

9. A method according to claim 3 wherein the α- or β-hydroxy carboxylic acid of step (iv) is present from 0.4 to 12%.

10. A method according to claim 9 wherein the α-hydroxy carboxylic acid of step (iv) is lactic acid and is present therein at 5%.

* * * * *